(12) United States Patent
Toms

(10) Patent No.: US 10,514,329 B1
(45) Date of Patent: Dec. 24, 2019

(54) AUTOSAMPLER WITH SAMPLE AGITATION SYSTEM

(71) Applicant: Elemental Scientific, Inc., Omaha, NE (US)

(72) Inventor: Andrew D. Toms, Guelph (CA)

(73) Assignee: Elemental Scientific, Inc., Omaha, NE (US)

( * ) Notice: Subject to any disclaimer, the term of this patent is extended or adjusted under 35 U.S.C. 154(b) by 282 days.

(21) Appl. No.: 15/228,044

(22) Filed: Aug. 4, 2016

Related U.S. Application Data

(60) Provisional application No. 62/202,395, filed on Aug. 7, 2015.

(51) Int. Cl.
*B01F 7/18* (2006.01)
*G01N 1/38* (2006.01)
*G01N 35/00* (2006.01)

(52) U.S. Cl.
CPC ............. *G01N 1/38* (2013.01); *B01F 7/18* (2013.01); *G01N 35/00722* (2013.01); *B01F 2215/0037* (2013.01); *G01N 2001/386* (2013.01); *G01N 2035/00534* (2013.01)

(58) Field of Classification Search
CPC ........................................................ B01F 7/18
USPC ................................. 366/285, 286, 601, 140
See application file for complete search history.

(56) References Cited

U.S. PATENT DOCUMENTS

| | | | | |
|---|---|---|---|---|
| 348,931 | A * | 9/1886 | Ross ..................... | B01F 7/161 366/286 |
| 3,194,542 | A * | 7/1965 | Pfeifer .................. | B01F 9/0016 366/235 |
| 4,403,867 | A * | 9/1983 | Duke ..................... | B01F 9/12 101/DIG. 34 |
| 4,527,904 | A * | 7/1985 | Weetman ............. | B01F 15/00207 318/466 |
| 4,668,096 | A * | 5/1987 | Saaty .................... | B29B 7/728 366/100 |
| 5,365,798 | A * | 11/1994 | Kressirer ............ | B01F 11/0088 366/140 |
| 9,302,234 | B2 * | 4/2016 | Misono ............... | B01F 13/0025 |
| 2002/0167861 | A1 * | 11/2002 | Barton ................. | A47J 43/082 366/142 |

(Continued)

OTHER PUBLICATIONS

Bortoli, Shane, "Sample Preparation System (SPS-5) and Diluter", Service Manual, Varian, Publication No. 8510110200, Jun. 1992, pp. 1-35.

*Primary Examiner* — David L Sorkin
(74) *Attorney, Agent, or Firm* — Kevin E. West; Advent, LLP

(57) ABSTRACT

A sample agitation system for an automated sampling device is described. In an example implementation, the sample agitation system includes a sample probe configured to contact a sample positioned within a sample vessel. Further, the sample agitation system includes an actuator coupled to the sample probe that is configured to stir the sample positioned within the sample vessel in one or more rotational directions. The directions may include, but are not limited to, clockwise motion, anti-clockwise motion, or the like. In some implementations, a sample probe support arm can be coupled to the sample probe and/or the actuator. The actuator can move the sample probe support arm in a translational, a rotational, and/or a vertical direction to rotate the sample probe and stir the sample.

16 Claims, 8 Drawing Sheets

(56) References Cited

U.S. PATENT DOCUMENTS

2007/0122312 A1* 5/2007 Chojnacki .............. B01F 11/04
                                                    422/561
2016/0195457 A1* 7/2016 Black .................... G01N 35/10
                                                    436/43

* cited by examiner

AUTOSAMPLER WITH SAMPLE AGITATION SYSTEM

CROSS-REFERENCE TO RELATED APPLICATIONS

The present application claims the benefit under 35 U.S.C. § 119(e) of U.S. Provisional Application Ser. No. 62/202,395, filed Aug. 7, 2015, and titled "AUTOSAMPLER WITH SAMPLE AGITATION SYSTEM," which is herein incorporated by reference in its entirety.

BACKGROUND

Many laboratory settings involve analyzing a large number of biochemical or chemical samples simultaneously. Mechanized sampling has been implemented and can be utilized to enhance efficiency of sample testing. This type of mechanized sampling is referred to as autosampling. Autosampling is achieved by using an automated sampling device known as an autosampler.

SUMMARY

A sample agitation system for an automated sampling device is described. In an example implementation, the sample agitation system includes a sample probe configured to contact a sample positioned within a sample vessel. Further, the sample agitation system includes an actuator coupled to the sample probe that is configured to stir the sample positioned within the sample vessel in one or more rotational directions. The directions may include, but are not limited to, clockwise motion, anti-clockwise motion, or the like. In some implementations, a sample probe support arm can be coupled to the sample probe and/or the actuator. The actuator can move the sample probe support arm in a translational, a rotational, and/or a vertical direction to rotate the sample probe and stir the sample.

Additionally, a method of agitating a sample is described. The method includes introducing a sample probe into a sample vessel and actuating the sample probe to rotationally oscillate within the sample vessel. In an embodiment, the method includes actuating the sample probe to rotationally oscillate in a clockwise or anti-clockwise direction.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

FIGURES

The Detailed Description is described with reference to the accompanying figures. The use of the same reference numbers in different instances in the description and the figures may indicate similar or identical items.

DETAILED DESCRIPTION

Overview

Often in laboratory settings, large numbers of samples are analyzed. Autosamplers can be used to facilitate the analysis of the sample compositions by removing samples from sample vessels for introduction to sample analysis systems. Uniformity throughout each sample can assist with providing more accurate test results by avoiding inaccuracies associated with concentration gradients within a sample. To achieve uniformity, samples containing immiscible liquids, partially dissolved samples, settling samples, or the like may need to be stirred or agitated prior to testing. Similarly, solid samples that must be placed in solution prior to testing may be heated, stirred, or the like. However, those methods increase the amount of time required to prepare the samples for testing. Therefore, to improve sample testing efficiency, a sample agitation system may be utilized. For example, a sample agitation system may provide laboratory personnel with an automated process to rapidly stir or mix a sample inside a sample vessel, while laboratory personnel perform other procedures. The automated mixing may shorten the amount of time needed by laboratory personnel to prepare the samples for testing, while also providing consistency in sample mixing.

Example Implementations

Figure 1:
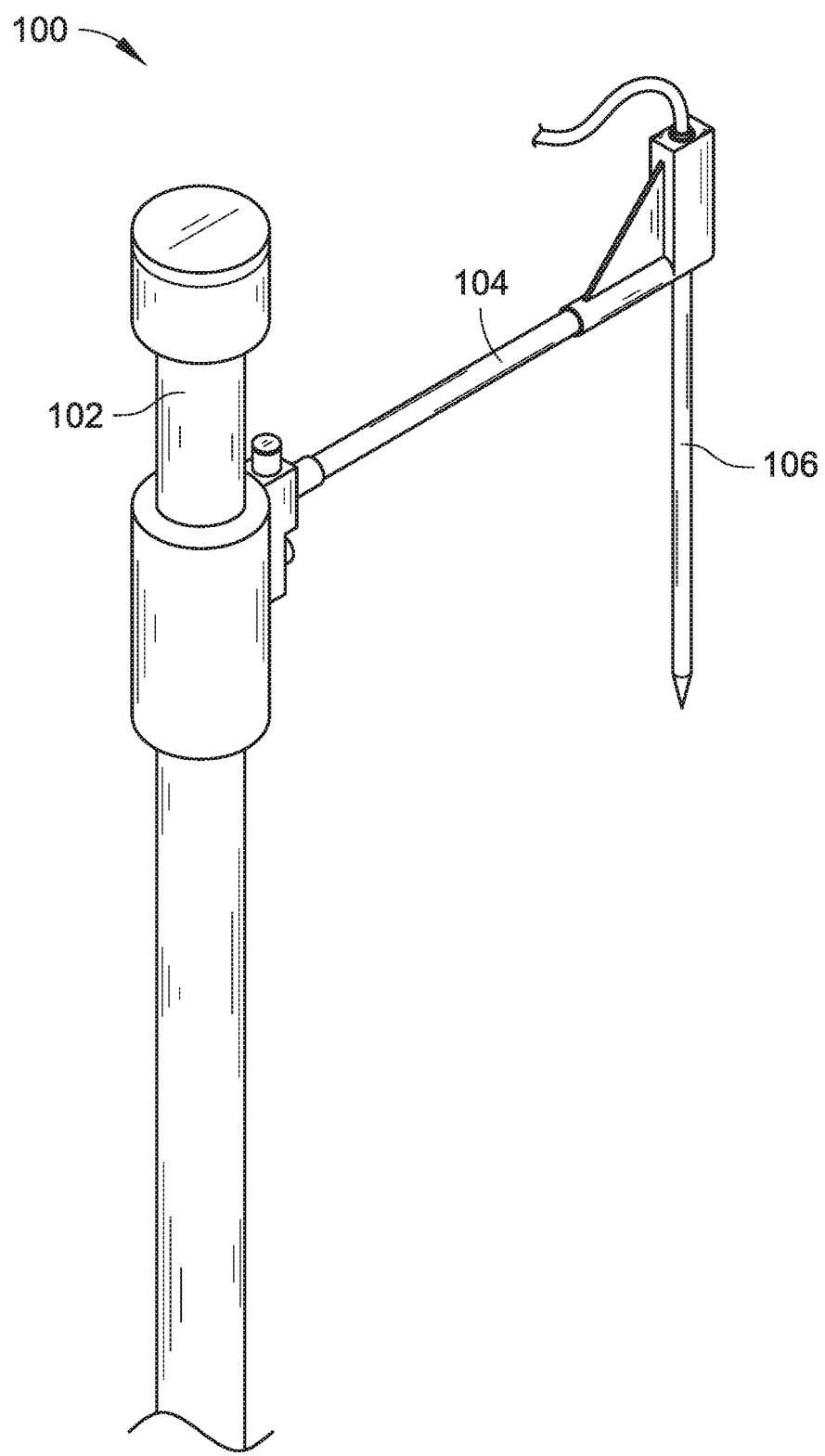
FIG. 1 is a partial isometric view of a sample probe for a sample agitation system for an automated sampling device in accordance with example implementations of the present disclosure.
Figure 2:
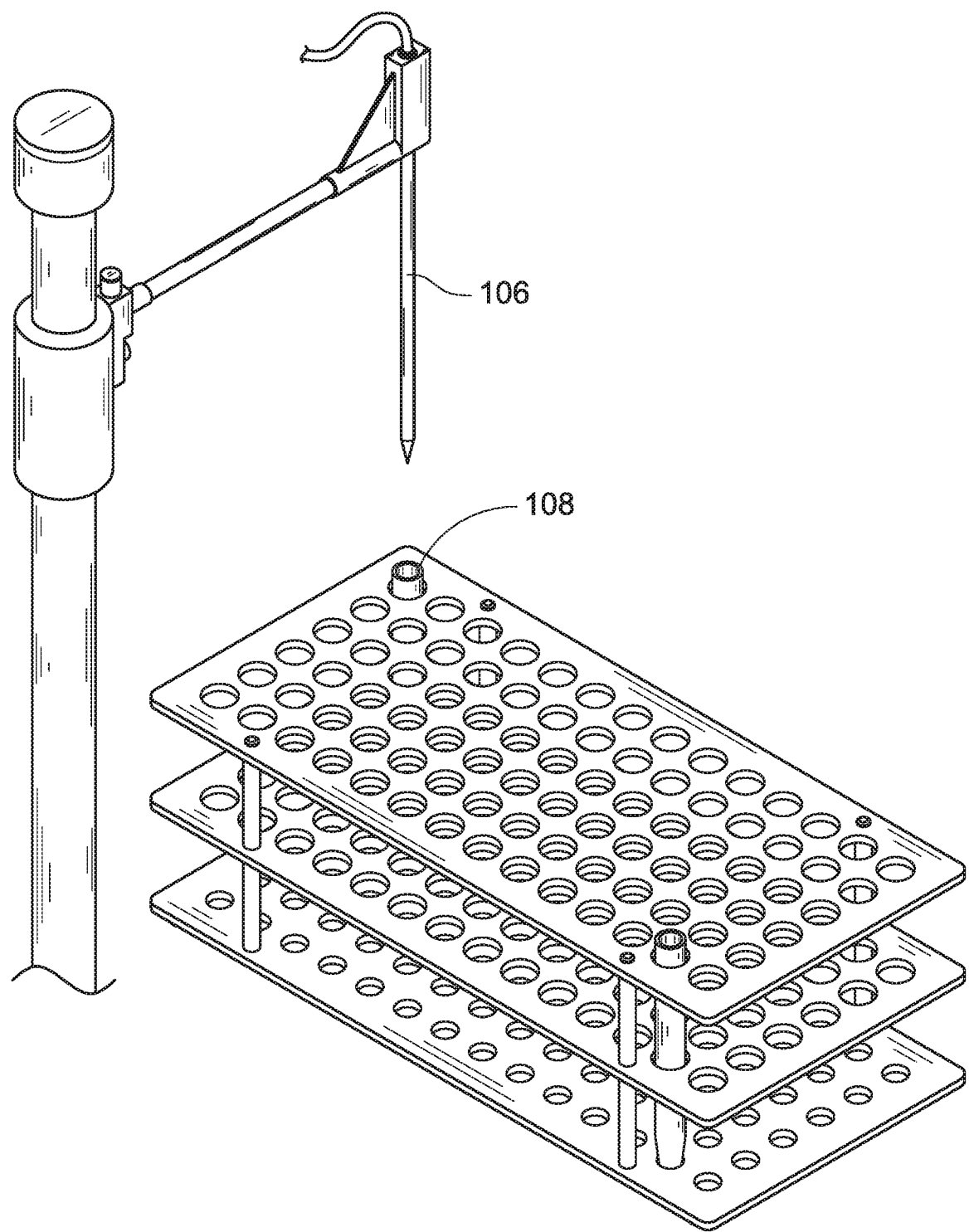
FIG. 2 is a partial isometric view of a sample probe positioned above a sample vessel having a sample contained therein.
Figure 3:
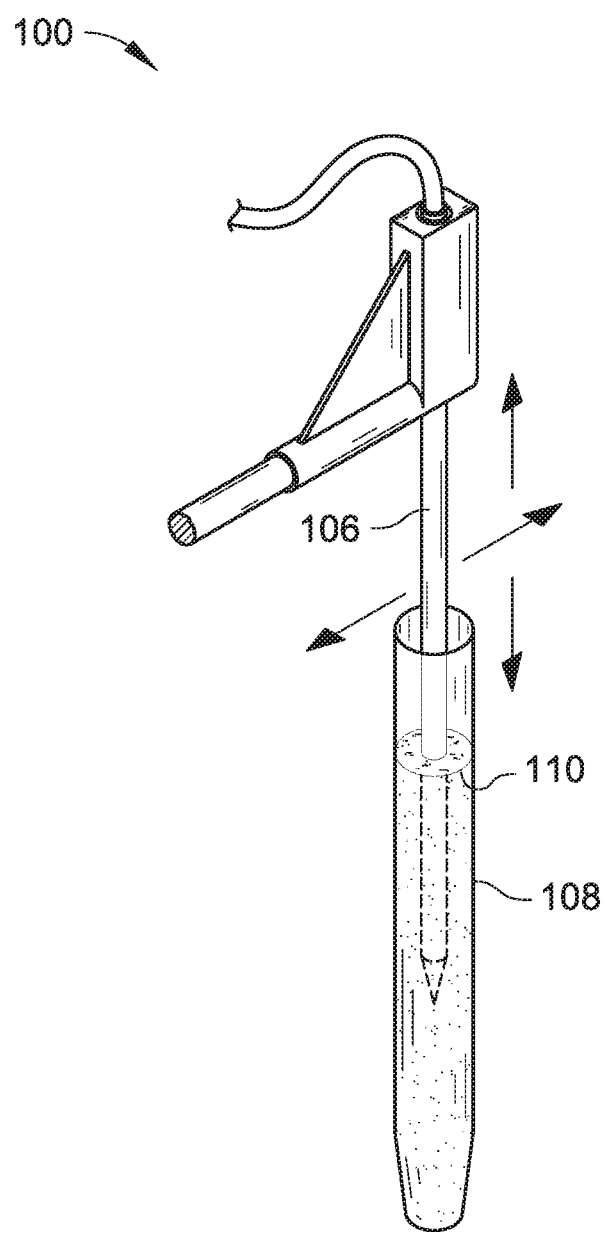
FIG. 3 is a diagrammatic illustration of a sample probe positioned within the sample vessel in contact with the sample in a ready state to stir or agitate the sample.

FIG. 1 illustrates a sample agitation system 100 of an automated sampling device in accordance with an example implementation of the present disclosure. The automated sampling device may be a part of, or may facilitate introduction of samples to a sample analysis instrument which can include, but is not limited to, a mass spectrometer, an inductively coupled plasma system, and a chromatography system. A sample agitation system 100 includes a z-axis support 102 attached to a sample probe support arm 104. As illustrated, the z-axis is aligned with gravity or a vertical axis. The sample probe support arm 104 is coupled to a sample probe 106 configured to aspirate a sample from a sample vessel (e.g., a sample vial, a microtiter plate, etc.). FIG. 2 depicts the sample probe 106 positioned above a sample vessel 108. In implementations, such as shown in FIG. 3, the sample probe support arm 104 maneuvers vertically about the z-axis support 102 to position the sample probe 106 within the sample vessel 108 to aspirate a sample therein for analysis in a sample analysis instrument. The sample probe support arm 104 can also move (e.g., via motor control) to introduce the sample probe 106 to various positions within the sample vessel 108. In some implementations, the sample probe 106 is mounted to the sample probe support arm 104, which is moved through space in three dimensions, or about an axis having y-motion that is a substantially rotary motion and along an axis having x-motion which is at least substantially horizontal linear motion or translation, and along a z-axis that is at least substantially vertical, for linear motion or translation.

In an implementation, the components of sample probe support arm 104 are formed of carbon composite materials. Further, all exposed surfaces of the sample probe support arm 104 are made from inert or fluoropolymer-covered materials (i.e., Teflon®). It should be understood, however, that the sample probe support arm 104 may be made with various materials, including aluminum, steel, plastic, and so forth.

Figure 4:
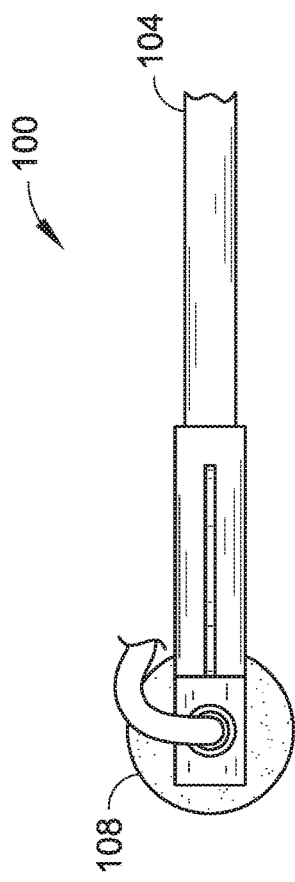
FIG. 4 is a top view of the sample probe positioned in the sample vessel.
Figure 6:
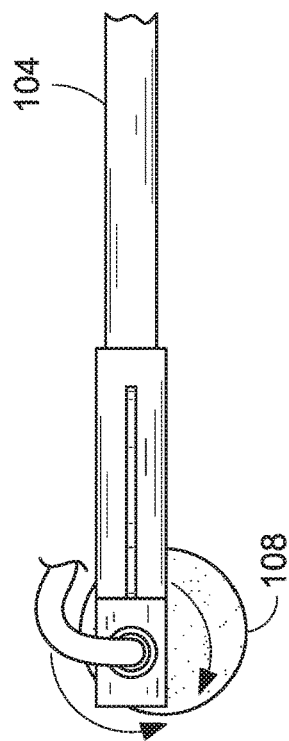
FIG. 6 is a top view of the sample probe actuated to stir the sample within the vessel via movement of the sample probe support arm in accordance with an example implementation of the present disclosure.
Figure 5:
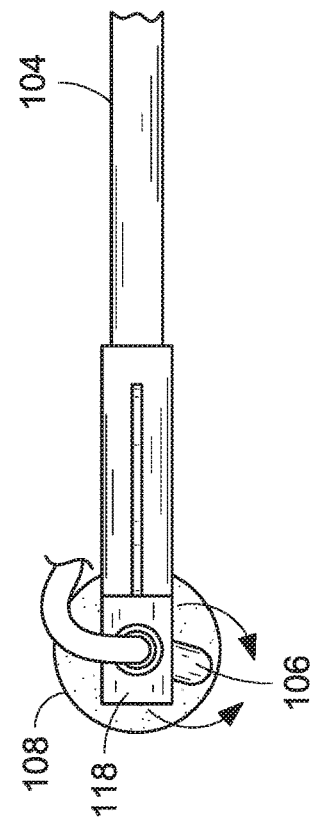
FIG. 5 is a top view of the sample probe actuated to oscillate in a direction within the sample vessel, including a motor assembly, in accordance with an example implementation of the present disclosure.
Figure 7:
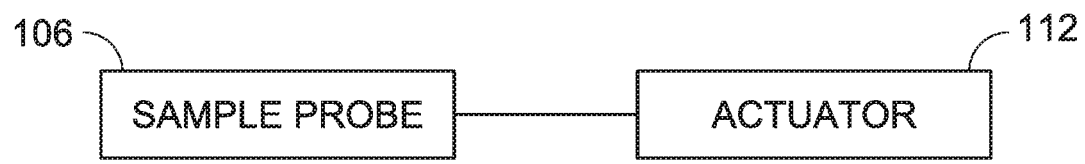
FIG. 7 is a schematic illustration of an actuator coupled to the sample probe.

FIG. 4 is a top view showing the sample probe support arm 104 positioned over the sample vessel 108 in accordance with example implementations of the sample agitation system 100. In an implementation, the sample probe 106 is actuated to move in a preprogrammed path and is positioned at an about ninety degree (90°) angle to the sample probe support arm 104, however the sample probe 106 may be at a different angle other than about ninety degrees (90°) from the sample probe support arm 104. FIG. 5 is a top view of the sample probe 106 introduced into the sample vessel 108, and the sample probe 106 moving in for example, but not limited to, a clockwise or anti-clockwise motion in accordance with example implementations of the sample agitation system 100. For example, alternative sample agitation motion may include moving in a path through the x, y and/or z planes. In implementations, the sample probe 106 remains stationary relative to the sample probe support arm 104. In implementations, the sample probe 106 rotates relative to the sample probe support arm 104 to provide a stirring motion independent of a motion of the sample probe support arm 104. For example, the sample agitation system 100 can include a motorized assembly 118 coupled to the sample probe 106 configured to rotate the sample probe 106 relative to the sample probe support arm 104. FIG. 6 shows the sample probe support arm 104 positioned to move the sample probe 106 within the sample vessel 108 in a clockwise or anti-clockwise motion. While the sample probe support arm 104 is shown moving the sample probe 106 in clockwise or anti-clockwise directions, other sample agitation motions may facilitated by the sample probe support arm 104, including, but not limited to, moving in any path through the x, y and/or z planes of the sample vessel 108. FIG. 7 illustrates the sample probe 106 coupled to an actuator 112. In implementations, the actuator 112 can execute preprogrammed instructions to move the sample probe 106 offset from an initial position within the sample vessel 108 to rotationally oscillate about the original position in a clockwise or anti-clockwise direction (or other directions throughout the x, y and/or z planes of the sample vessel 108) to agitate the sample. In implementations, oscillation of the sample probe 106 includes rapid oscillation that moves the sample probe 106 at a rate that exceeds the rate of normal movement of the sample probe support arm 104. Following the agitation, the actuator 112 can return the sample probe 106 to its original position to prepare the sample probe 106 for aspiration of the sample.

Figure 8:
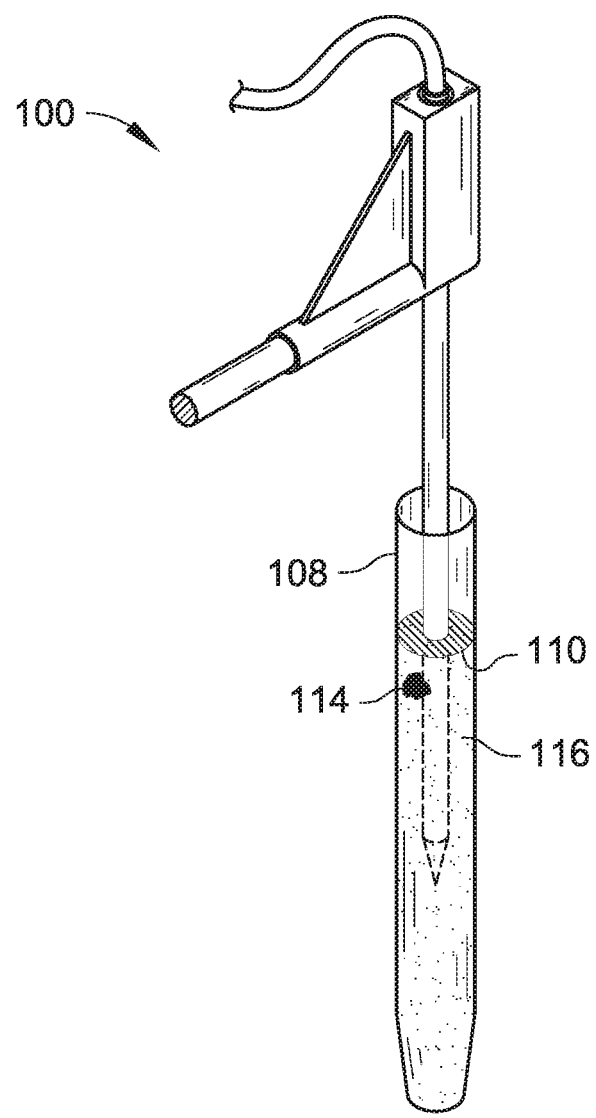
FIG. 8 is a diagrammatic illustration of a sample agitation system contacting the sample comprising a liquid and a solid.
Figure 10:
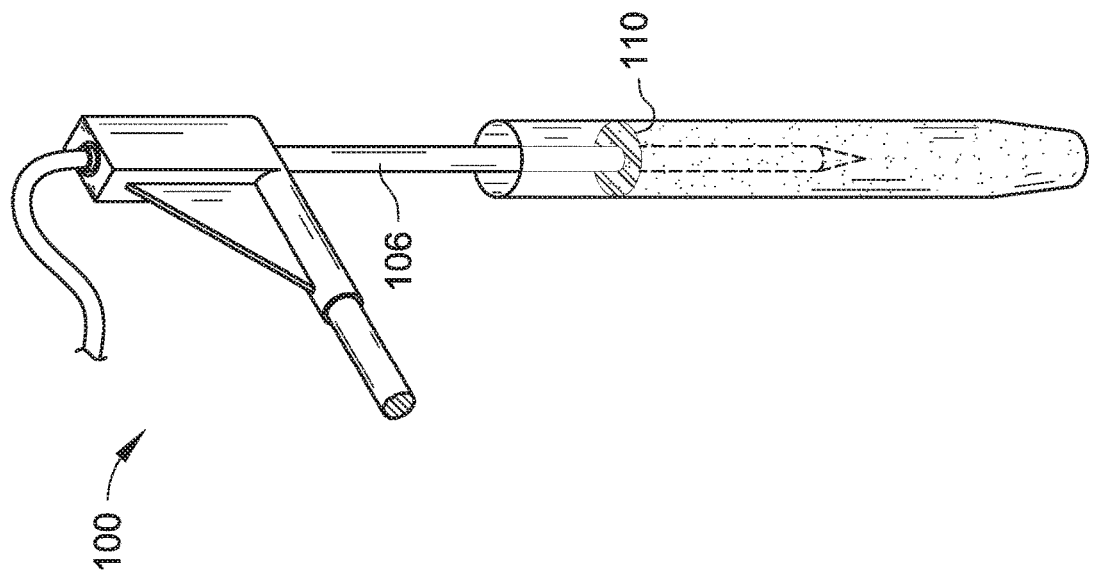
FIG. 10 is a diagrammatic illustration of a substantially uniform sample having the solid dissolved into solution, with the sample agitation system removing the probe from the sample vessel after agitating the sample.
Figure 9:
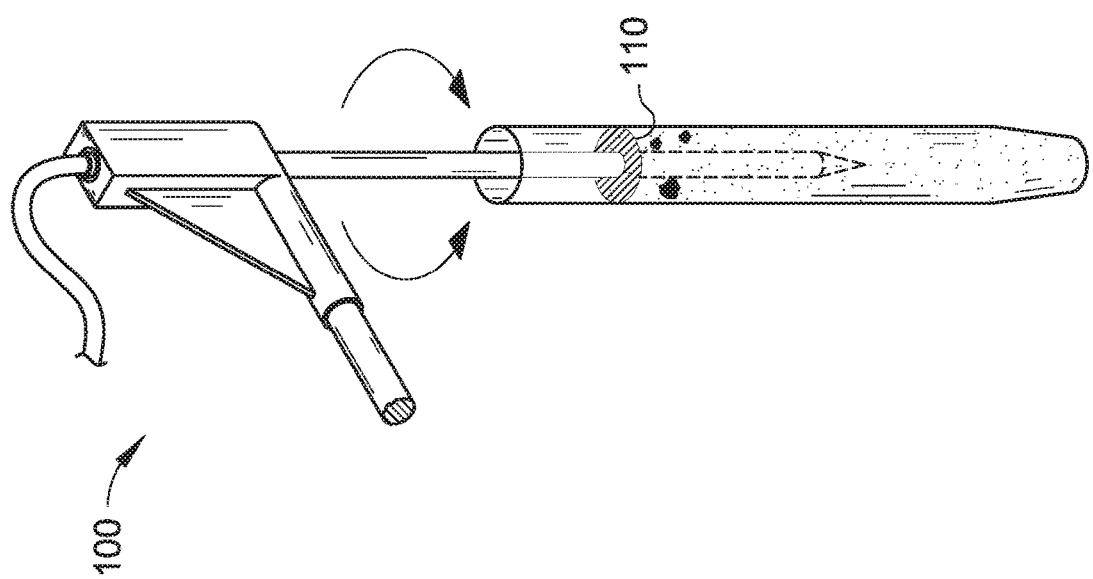
FIG. 9 is a diagrammatic illustration of a sample agitation system actuated to move in a preprogrammed direction causing the solid to go into solution.

FIG. 8 shows the sample probe 106 positioned within the sample vessel 108 and contacting a sample 110. As shown the sample 110 includes a solid portion 114 and a liquid portion 116. The sample agitation system 100 can agitate the sample 110 to dissolve at least a portion of the solid portion in solution by agitation. For instance, as shown in FIG. 9, sample agitation by the sample agitation system 100 may include, but is not limited to, clockwise motion, anti-clockwise motion, motion in any path through the x, y and/or z planes of the sample vessel 108, or the like. FIG. 9 shows the solid portion of the sample being dispersed into solution by agitation from the sample agitation system 100. In other embodiments, the sample 110 may include, for example, an immiscible liquid that includes a gas phase and a liquid phase or multiple liquid phases. FIG. 10 shows an example of the sample 110 uniformly mixed following agitation by the sample agitation system 100, where the sample probe 106 is returned to its original position.

Figure 11:
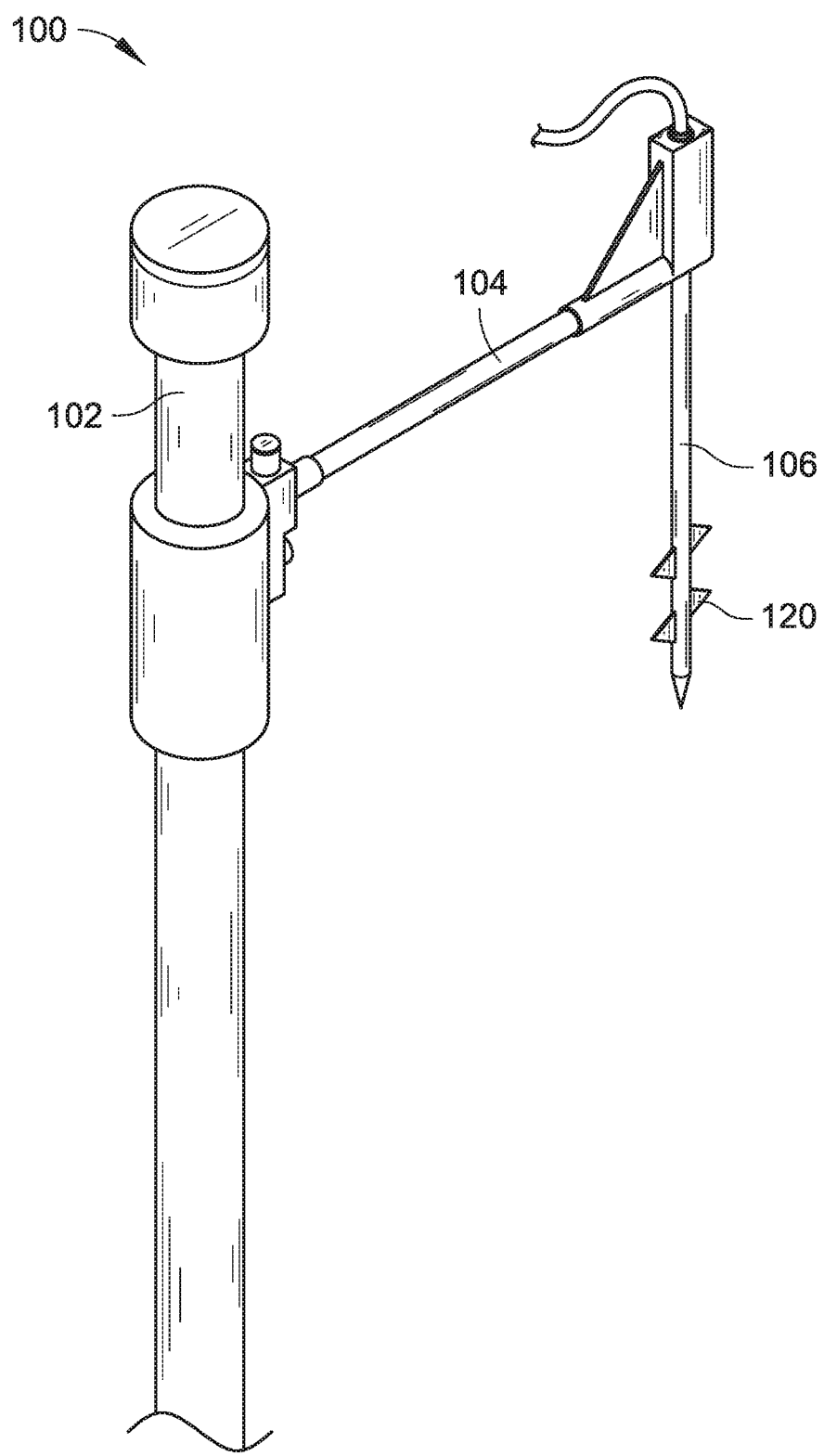
FIG. 11 is a partial isometric view of a sample probe for a sample agitation system for an automated sampling device, further including structures for inducing or increasing agitation in the sample, in accordance with example implementations of the present disclosure.

In another implementation, structures 120 on an outer surface of the sample probe 106 may be included, as illustrated in FIG. 11. These structures 120 may include vanes, ridges, fins, adapters, paddles, or the like that may be positioned on the outer surface of the sample probe 106. While FIG. 11 shows four structures 120 (e.g., triangular fins) positioned on the outer surface of the sample probe 106, the sample agitation system 100 can use any number of structures 120 (e.g., one, two, three, four, more than four, etc.) to provide a specific agitation pattern, sample vortex size, shape duration, or the like duration rotational oscillation of the sample probe 106 within the sample vessel 108. The structures 120 can be applied to the sample probe 106 through, for example, molding, etching, attachment, or the like. Additionally, these structures 120 may induce or aid agitation of the sample as the sample probe 106 is actuated in the axis motion previously described. For instance, the structures 120 may agitate the sample 110 when the sample probe 106 is actuated vertically along the z-axis, horizontally through the x-y plane, or combinations thereof. In general, the structures 120 are fractionally smaller than the diameter of the sample vessel 108, allowing the sample probe 106 to enter the sample vessel 108 with the structures 120 to permit the rotational oscillation of the sample probe 106 within the sample vessel 108 (e.g., avoiding contact of the structures 120 on the interior sample vessel walls). In an implementation, a portion of the structure 120 is offset relative to the z-axis to facilitate vortex generation within the sample within the sample vessel 108, such as during vertical motion of the sample probe 106 within the sample vessel 108.

In implementations, the sample agitation system 100 can actuate the sample probe 106 to prepare the sample 110 for aspiration. For example, the sample probe 106 can be actuated prior to aspiration of the sample 110 in order to achieve uniformity of the sample composition, which in turn can provide for more accurate testing results.

Figure 12A:
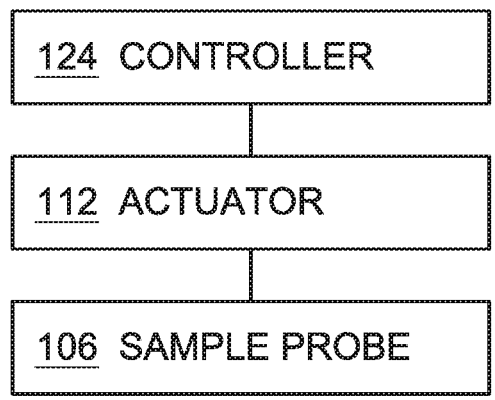
FIG. 12A is a block diagram illustration of a sample agitation system including a controller in accordance with example implementations of the present disclosure.
Figure 12B:
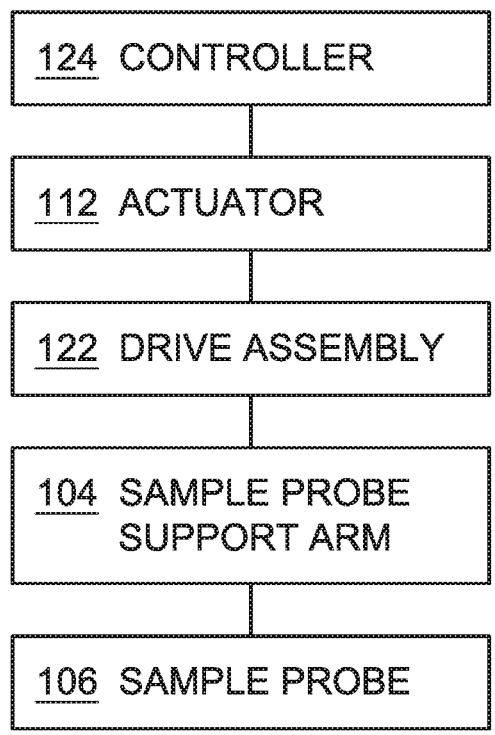
FIG. 12B is a block diagram illustration of a sample agitation system including a controller and a drive assembly in accordance with example implementations of the present disclosure.

In some implementations, the sample agitation system 100 includes z-axis support 102 attached to drive assembly 122, sample probe support arm 104 attached to z-axis support 102, and sample probe 106 attached to sample probe support arm 104. The sample agitation system 100 is controlled by a controller 124 that is operably coupled to the drive assembly 122 and/or the actuator 112, as illustrated in FIGS. 12A and 12B. In an implementation, the drive assembly 122 causes the sample probe support arm 104 to move along a center slot in an autosampler device, in translation along an axis coaxial to z-axis support 102, and radially about the z-axis for inserting sample probe 106 into a sample vessel 108. The drive assembly 122 can include one or more motors (e.g., stepper motors) to control translation, angular rotation, and/or vertical movement of the sample probe support arm 104. The drive assembly 122 can also include a linear drive (e.g., a worm drive). Further, in accordance with the present disclosure, the drive assembly 118 and/or the actuator 112 may be hard-wired or, in another implementation, controlled via wireless communication. Thus, wireless communications may be used to connect controller 124 with the desired analytical instrument (not shown). Utilization of wireless communications allows sample assaying to occur without requiring physical connection with a controller computer increasing mobility of the automated sampling device. In some implementations, the drive assembly 122 and/or the actuator 112 can receive programmed instructions from the controller 124. The programmed instructions can be based on user parameters. For example, a user can select timing intervals for agitation based on the type or nature of the sample (e.g., increased agitation time for viscous samples). Other user parameters can include, but are not necessarily limited to: agitation speed and direction (e.g., clockwise, anti-clockwise, vertical, combinations thereof, etc.).

The clockwise and anti-clockwise motion described previously may be attributable to one or more of the axis-motions explained above. For example, in an implementation, the actuator 112 is configured to move the sample probe 106 according to one or more of the motions described above to provide sample agitation. In some implementations, the actuator 112 is configured to move the sample probe support arm 104 according to one or more of the motions described above to provide sample agitation. For example, the actuator 112 can be coupled to the drive assembly 122 and can cause the drive assembly 122 to move the sample arm assembly in a translational, rotational, and/or vertical direction to provide sample agitation (see FIGS. 6 and 12B).

A sample agitation system 100 of an automated sampling device, including some or all of its components, can operate under computer control. For example, a processor can be included with or in a sample agitation system 100 to control the components and functions of systems 100 described herein using software, firmware, hardware (e.g., fixed logic circuitry), manual processing, or a combination thereof. The terms "controller," "functionality," "service," and "logic" as used herein generally represent software, firmware, hardware, or a combination of software, firmware, or hardware in conjunction with controlling the systems 100. In the case of a software implementation, the module, functionality, or logic represents program code that performs specified tasks when executed on a processor (e.g., central processing unit (CPU) or CPUs). The program code can be stored in one or more computer-readable memory devices (e.g., internal memory and/or one or more tangible media), and so on. The structures, functions, approaches, and techniques described herein can be implemented on a variety of commercial computing platforms having a variety of processors.

A processor provides processing functionality for the system 100 and can include any number of processors, micro-controllers, or other processing systems, and resident or external memory for storing data and other information accessed or generated by the system 100. The processor can execute one or more software programs that implement techniques described herein. The processor is not limited by the materials from which it is formed or the processing mechanisms employed therein and, as such, can be implemented via semiconductor(s) and/or transistors (e.g., using electronic integrated circuit (IC) components), and so forth.

The system 100 also includes a memory. The memory is an example of tangible, computer-readable storage medium that provides storage functionality to store various data associated with operation of the system 100, such as software programs and/or code segments, or other data to instruct the processor, and possibly other components of the system 100, to perform the functionality described herein. Thus, the memory can store data, such as a program of instructions for operating the system 100 (including its components), and so forth. It is noted that while a single memory is described, a wide variety of types and combinations of memory (e.g., tangible, non-transitory memory) can be employed. The memory can be integral with the processor, can comprise stand-alone memory, or can be a combination of both. The memory can include, but is not necessarily limited to: removable and non-removable memory components, such as random-access memory (RAM), read-only memory (ROM), flash memory (e.g., a secure digital (SD) memory card, a mini-SD memory card, and/or a micro-SD memory card), magnetic memory, optical memory, universal serial bus (USB) memory devices, hard disk memory, external memory, and so forth. In implementations, the system 100 and/or the memory can include removable integrated circuit card (ICC) memory, such as memory provided by a subscriber identity module (SIM) card, a universal subscriber identity module (USIM) card, a universal integrated circuit card (UICC), and so on.

The system 100 includes a communications interface. The communications interface is operatively configured to communicate with components of the system 100. For example, the communications interface can be configured to transmit data for storage in the system 100, retrieve data from storage in the system 100, and so forth. The communications interface is also communicatively coupled with the processor to facilitate data transfer between components of the system 100 and the processor (e.g., for communicating inputs to the processor received from a device communicatively coupled with the system 100 and/or communicating output to a device communicatively coupled with the system 100. It is noted that while the communications interface is described as a component of a system 100, one or more components of the communications interface can be implemented as external components communicatively coupled to the system 100 via a wired and/or wireless connection. The system 100 can also comprise and/or connect to one or more input/output (I/O) devices (e.g., via the communications interface) including, but not necessarily limited to: a display, a mouse, and so on.

The communications interface and/or the processor can be configured to communicate with a variety of different networks including, but not necessarily limited to: a wide-area cellular telephone network, such as a 3G cellular network, a 4G cellular network, or a global system for mobile communications (GSM) network; a wireless computer communications network, such as a WiFi network (e.g., a wireless local area network (WLAN) operated using IEEE 802.11 network standards); an internet; the Internet; a wide area network (WAN); a local area network (LAN); a personal area network (PAN) (e.g., a wireless personal area network (WPAN) operated using IEEE 802.15 network standards); a public telephone network; an extranet; an intranet; and so on. However, this list is provided by way of example only and is not meant to limit the present disclosure. Further, the communications interface can be configured to communicate with a single network or multiple networks across different access points.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

While the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A sample agitation system for an automated sampling device, comprising:
   a sample probe configured to contact a sample positioned within a sample vessel and configured to aspirate the sample from the sample vessel;
   a sample probe support arm coupled to the sample probe and configured to move the sample probe to one or more translational positions proximate to the sample vessel, the sample probe support arm angled relative to the sample probe; and
   an actuator coupled to the sample probe via the sample probe support arm, the actuator configured to move the sample probe in one or more rotational directions relative to the sample vessel to stir the sample positioned within the sample vessel.

2. The sample agitation system of claim 1, wherein the actuator is configured to move the sample probe in at least one of a clockwise direction or an anti-clockwise direction relative to the sample vessel.

3. The sample agitation system of claim 1, further including a drive assembly operably coupled to the actuator, the drive assembly configured to move the sample probe support arm in at least one of a translational, a rotational, or a vertical direction to stir the sample.

4. The sample agitation system of claim 1, further including a controller operably coupled to the actuator, the controller configured to cause the actuator to execute at least one programmed instruction based on a user parameter.

5. The sample agitation system of claim 4, wherein the user parameter includes at least one of an agitation speed, an agitation time interval, or an agitation direction.

6. The sample agitation system of claim 1, wherein the sample probe includes one or more structures positioned on an outer surface of the sample probe, the one or more structures configured to induce or increase stirring of the sample during motion of the sample probe.

7. The sample agitation system of claim 6, wherein the at least one structure of the one or more structures includes a portion that is offset relative to a z-axis.

8. A sample agitation system for an automated sampling device, comprising:
   a sample probe configured to contact a sample positioned within a sample vessel and configured to aspirate the sample from the sample vessel;
   a sample probe support arm coupled to the sample probe and configured to move the sample probe to one or more translational positions proximate to the sample vessel, the sample probe support arm angled relative to the sample probe; and
   an actuator coupled to the sample probe via the sample probe support arm, the actuator configured to rotate the sample probe and to stir the sample positioned within the sample vessel in at least one of a clockwise direction or an anti-clockwise direction relative to the sample vessel.

9. The sample agitation system of claim 8, further including a drive assembly operably coupled to the actuator, the drive assembly configured to move the sample probe support arm in at least one of a translational, a rotational, or a vertical direction to rotate the sample probe.

10. The sample agitation system of claim 8, further including a controller operably coupled to the actuator, the controller configured to cause the actuator to execute at least one programmed instruction based on a user parameter.

11. The sample agitation system of claim 10, wherein the user parameter includes at least one of an agitation speed, an agitation time interval, or an agitation direction.

12. The sample agitation system of claim 8, wherein the sample probe includes one or more structures positioned on an outer surface of the sample probe, the one or more structures configured to induce or increase stirring of the sample during motion of the sample probe.

13. The sample agitation system of claim 1, wherein the sample probe support arm is positioned at a first angle relative to the sample probe.

14. The sample agitation system of claim 13, wherein the first angle is about 90 degrees.

15. The sample agitation system of claim 8, wherein the sample probe support arm is positioned at a first angle relative to the sample probe.

16. The sample agitation system of claim 15, wherein the first angle is about 90 degrees.

* * * * *